US009260748B2

(12) United States Patent
Hamamah et al.

(10) Patent No.: US 9,260,748 B2
(45) Date of Patent: Feb. 16, 2016

(54) METHODS FOR ASSESSING ENDOMETRIUM RECEPTIVITY OF A PATIENT

(75) Inventors: Samir Hamamah, Montpellier (FR); Delphine Haouzi, Montpellier (FR)

(73) Assignee: Institut National de la Santé et de la Recherche Médicale, Paris (FR)

( * ) Notice: Subject to any disclaimer, the term of this patent is extended or adjusted under 35 U.S.C. 154(b) by 131 days.

(21) Appl. No.: 13/699,814

(22) PCT Filed: May 27, 2011

(86) PCT No.: PCT/EP2011/058757
§ 371 (c)(1),
(2), (4) Date: Nov. 26, 2012

(87) PCT Pub. No.: WO2011/147976
PCT Pub. Date: Dec. 1, 2011

(65) Prior Publication Data
US 2013/0072748 A1    Mar. 21, 2013

Related U.S. Application Data

(60) Provisional application No. 61/354,310, filed on Jun. 14, 2010.

(30) Foreign Application Priority Data

May 27, 2010    (EP) .................................... 10305561

(51) Int. Cl.
*C12Q 1/68*    (2006.01)
*A61B 17/435*    (2006.01)
*C40B 40/08*    (2006.01)

(52) U.S. Cl.
CPC ............ *C12Q 1/6837* (2013.01); *A61B 17/435* (2013.01); *C12Q 1/6883* (2013.01); *C40B 40/08* (2013.01); *C12Q 2600/158* (2013.01)

(58) Field of Classification Search
CPC .... A61B 17/425–17/435; A61D 19/00–19/04; B01J 19/0046; C12Q 1/6844–1/6867
USPC ....................................................... 600/33–35
See application file for complete search history.

(56) References Cited

U.S. PATENT DOCUMENTS

| 6,196,965 B1 * | 3/2001 | Purdum .......................... 600/34 |
| 2003/0175714 A1 * | 9/2003 | Kamme et al. .................... 435/6 |
| 2008/0064100 A1 | 3/2008 | Vacher et al. |

OTHER PUBLICATIONS

Simón C et. al. Coculture of Human Enbryos with Autologous Human Endometrial Epithelial Cells in Patients with Implantation Failure. The Journal of Clinical Endocrinology & Metabolism. vol. 84, p. 2638-2646, 1999.*

(Continued)

*Primary Examiner* — Catherine B Kuhlman
(74) *Attorney, Agent, or Firm* — Whitham, Curtis, Christofferson & Cook, P.C.

(57) ABSTRACT

The present invention relates to a method for assessing the endometrium receptivity of a patient, comprising a step consisting of measuring the expression level of eleven genes in an endometrial biopsy sample obtained from said patient wherein said genes are MFAP5, ANGPTL1, PROK1, NLF2, LAMB3, BCL2L10, CD68, TRPC4, SORCS1, FST and KRT80.

4 Claims, 8 Drawing Sheets

(56) References Cited

OTHER PUBLICATIONS

Figure 1:
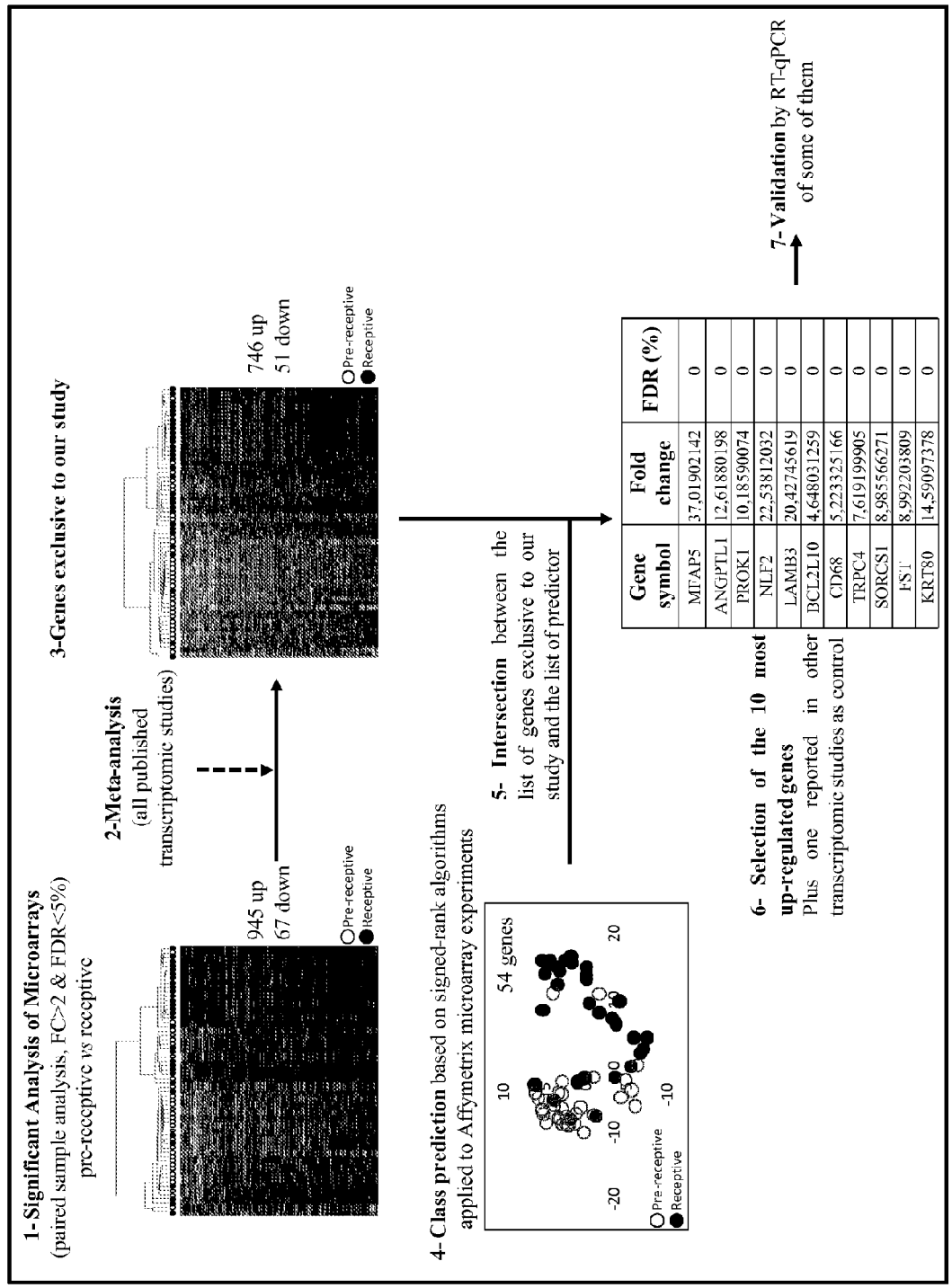

Haouzi D. et. al. Identification of new biomarkers of human endometrial receptivity in the natural cycle. Human Reproduction vol. 24, No. 1, p. 1980205, 2009.*

Simón C et al. Coculture of human embryos with autologous human endometrial epithelial cells in Patients with Implantation Failure. Journal of Clinical Endocrinology & Metabolism 84: 2638-2646, 1999).*

Spandorfer et al., "Autologous Endometrial Coculture in Patients with IVF Failure: Outcome of the First 1,030 Cases", Journal of Reproductive Medicine, Jun. 1, 2004, pp. 463-467, vol. 49, No. 6, US.

Haouzi et al., "Identification of new biomarkers of human endometrial receptivity in the natural cycle", Human Reproduction, Jan. 2009, pp. 198-205, vol. 24, No. 1.

Haouzi et al., "Human endometrial receptivity: comparison between natural and stimulated cycles for the same patients", Fertility and Sterility, Sep. 1, 2009, p. S56, Elsevier Science, Inc, New York.

Carson et al., "Changes in gene expression during the early to mid-luteal (receptive phase) transition in human endometrium detected by high-density microarray screening", Molecular Human Reproduction, Sep. 2002, pp. 871-879, vol. 8, No. 9, Oxford University Press.

Riesewijk et al., "Gene expression profiling of human endometrial receptivity on days LH+2 versus LH+7 by microarray technology", Molecular Human Reproduction, May 1, 2003, pp. 253-264, vol. 9, No. 5, Oxford University Press.

Mirkin et al., "In search of candidate genes critically expressed in the human endometrium during the window of implantation", Human Reproduction, Aug. 2005, pp. 2104-2117, vol. 20, No. 8, Oxford.

Talbi et al., "Molecular Phenotyping of Human Endometrium Distinguishes Menstrual Cycle Phases and Underlying Biological Processes in Normo-Ovulatory Women", Endocrinology, Mar. 2006, pp. 1097-1121, vol. 147, No. 3.

* cited by examiner

PR : pre-receptif sample (LH+2)
R : receptif sample (LH+7)

PR : pre-receptif sample (hCG+2)
R : receptif sample (hCG+5)

PR : pre-receptif sample (hCG+2)
R : receptive sample (hCG+5)

PR : pre-receptif sample (LH+2)
R : receptif sample (LH+7)

METHODS FOR ASSESSING ENDOMETRIUM RECEPTIVITY OF A PATIENT

FIELD OF THE INVENTION

The present invention relates to methods for assessing the endometrium receptivity of a patient.

BACKGROUND OF THE INVENTION

Despite many advances in assisted reproductive technology (ART), implantation rates are still low after controlled ovarian hyperstimulation (COH) and in vitro fertilization (IVF). It is assumed that two-thirds of implantation failures are associated with inadequate endometrium receptivity or with defects in the embryo-endometrium dialogue. The endometrium is receptive to blastocyst implantation during a spatially and temporally restricted window, called "the implantation window". In humans, this period begins 6-10 days after the LH surge and lasts approximately 48 hours. Several parameters have been suggested for assessing endometrium receptivity, including endometrial thickness which is a traditional criterion, endometrial morphological aspect and endometrial and subendometrial blood flow. However, their positive predictive value is still limited.

More recently, transcriptomic approaches have been driven to identify bio-markers of the human implantation window. Using microarray technology in human biopsy samples, several authors have observed modifications in gene expression profile associated to the transition of the human endometrium from a pre-receptive (early-secretory phase) to a receptive (mid-secretory phase) state (Carson et al., 2002; Riesewijk et al., 2003; Mirkin et al., 2005; Talbi et al., 2006). However, among the various regulated genes, only two genes were in common between all these studies (Haouzi et al., 2009). Such variability in the results with the same approach may have several explanations: differences in the day of the endometrial biopsies, different patient profiles, and inadequate numbers of endometrial samples studied (n≤11). In addition, only one study compared the early and the mid-secretory phase in the same patient (Riesewijk et al., 2003), which seems to us a necessary condition to minimize the impact of inter-patient variability.

Therefore, there is still a need in the ART for reliable biomarkers of the human endometrium receptivity that will help improving the clinical outcome of IVF.

SUMMARY OF THE INVENTION

The present invention relates to a method for assessing the endometrium receptivity of a patient, comprising a step consisting of measuring the expression level of eleven genes in an endometrial biopsy sample obtained from said patient wherein said genes are MFAP5, ANGPTL1, PROK1, NLF2, LAMB3, BCL2L10, CD68, TRPC4, SORCS1, FST and KRT80.

DETAILED DESCRIPTION OF THE INVENTION

The inventors aimed at identifying genes expressed in human endometrium during the implantation window that could be used as such markers. A series of normal responder patients (n=31) underwent endometrial biopsies (n=62) during the early-secretory phase (LH+2) and the mid-secretory phase (LH+7) of the same natural cycle, that preceded a new intra cytoplasmic sperm injection (ICSI) attempt for male infertility factor. Samples were analyzed using DNA microarrays and microarray analyses were performed by paired samples between the early- and the mid-secretory stages for each patient, which is essential to minimize the inter-patient variability. To identify new markers of endometrium receptivity, the inventors have first intersected the gene list significantly modulated between the LH+2 and LH+7 sample groups with those from four other transcriptomic studies which compared the same natural endometrium cycle phases (Carson et al., 2002; Riesewijk et al., 2003; Mirkin et al., 2005; Talbi et al., 2006) to identify a list of genes comprising 797 genes specifically modulated during the implantation window and exclusive to the present study (FIG. 1). Hierarchical clustering with these data (797 genes) revealed that this list allowed a clear segregation of the two endometrium sample groups and FIG. 1 illustrates this separation. Interestingly, the majority of these genes were up-regulated during the implantation window (746 up-regulated genes, 51 down-regulated genes) (FIG. 1).

A new approach for class prediction applied to microarray experiments was then used to identify biomarkers putatively involved in endometrial receptiveness. To select candidate genes of the implantation window, the inventors then have compared the list of genes specifically modulated during the implantation window and exclusive to the study with the list of predictor. The inventors have therefore selected the 10 most-up-regulated new genes predicting endometrium receptivity, not listed in reports by microarray analysis. Among these new genes, 4 genes have been published in Haouzi et al. (2009). These published biomarkers are MFAP5 (microfibrillar associated protein 5), ANGPTL1 (angiopoietin-like 1), EG-VEGF also called PROK1 (endocrine-gland-derived vascular endothelial growth factor or prokineticin 1) and NLF2 also called C2CD4B (nuclear localized factor 2 or C2 calcium-dependent domain containing 4B) and are all overexpressed during the implantation window in microarray analyses respectively by a factor of 37, 12.6, 10.2, and 22.5 (Table A). In addition, a gene found in other microarray analyses was chosen as a positive control of human endometrium receptivity: LAMB3 (laminin beta 3). The six unpublished genes were BCL2L10 (BCL2-like 10), CD68 antigen, TRPC4 (transient receptor potential cation channel, subfamily C, member 4), SORCS1 (sortilin-related VPS10 domain containing receptor 1), FST (follistatin), and KRT80 (keratin 80) which were also over-expressed during the implantation window by a factor 4.7, 5.3, 7.7, 9, 9 and 14.6 respectively (Table A). Conclusion: Eleven genes (MFAP5, ANGPTL1, PROK1, NLF2, LAMB3, BCL2L10, CD68, TRPC4, SORCS1, FST and KRT80) have been selected for the first time and represent new biomarkers for exploration of endometrial receptiveness. As the endometrial biopsy is an easy procedure to perform during a natural cycle, the present invention represents accordingly a novel strategy in patients with poor implantation after IVF or ICSI.

Accordingly the present invention relates to a method for assessing the endometrium receptivity of a patient, comprising a step consisting of measuring the expression level of eleven genes in an endometrial biopsy sample obtained from said patient wherein said genes are MFAP5, ANGPTL1, PROK1, NLF2, LAMB3, BCL2L10, CD68, TRPC4, SORCS1, FST and KRT80.

As used herein the term "patient" refers to a mammalian female to which the present invention may be applied. Typically said mammal is a human (i.e a woman), but may concern other mammals such as primates, dogs, cats, pigs, sheep, cows . . . .

All the genes pertaining to the invention are known per se, and are listed in the below Table A.

TABLE A

Set of predictive genes.

| Gene Symbol | Gene name | Gene ID | Fold change |
|---|---|---|---|
| MFAP5 | microfibrillar associated protein 5 | 8076 | 37.01902142 |
| ANGPTL1 | angiopoietin-like 1 | 9068 | 12.61880198 |
| PROK1 | endocrine-gland-derived vascular endothelial growth factor or prokineticin 1 | 84432 | 10.18590074 |
| NLF2 | nuclear localized factor 2 or C2 calcium-dependent domain containing 4B | 388125 | 22.53812032 |
| LAMB3 | laminin, beta 3 | 3914 | 20.42745619 |
| BCL2L10 | BCL2-like 10 | 10017 | 4.648031259 |
| CD68 | CD68 antigen | 968 | 5.223325166 |
| TRPC4 | transient receptor potential cation channel, subfamily C, member 4 | 7223 | 7.619199905 |
| SORCS1 | sortilin-related VPS10 domain containing receptor 1 | 114815 | 8.985566271 |
| FST | follistatin | 10468 | 8.992203809 |
| KRT80 | keratin 80 | 144501 | 14.59097378 |

The methods of the invention may further comprise a step consisting of comparing the expression level of the genes in the endometrial biopsy sample with a control, wherein detecting differential in the expression level of the genes between the endometrial biopsy sample and the control is indicative whether the endometrium is receptive. The control may consist in an endometrial biopsy sample obtained form a receptive endometrium or may consist of an endometrial biopsy sample obtained form a non-receptive endometrium.

In a preferred embodiment, the patient has observed a natural cycle. The inventors indeed believe that stimulated cycle or natural modified cycle has an impact on endometrium receptivity. The term "natural cycle" refers to the natural cycle by which the female or patient produces one oocyte. The term "modified natural cycle" refers to the process by which, the female or patient produces between two and five oocytes under a mild ovarian stimulation with GnRH antagonists associated with recombinant FSH or hMG. The term "stimulated cycle" refers to the process by which a female or a patient produces more than one oocyte under stimulation with GnRH agonists or antagonists associated with recombinant FSH or hMG. The inventors have indeed observed that gonadotrophin treatments in controlled ovarian hyperstimulation (COS) cycles led to disruptions of the transcriptional activation of genes involved in normal endometrium receptivity. Accordingly, the present invention opens new perspectives, particularly in patients with multiple implantation failures. In this case, analysis of the endometrial profile could reveal a strongly altered profile during COS protocols, prompting the clinician to either adapt the IVF stimulation protocol or to perform embryo transfer later during a natural cycle. More particularly, when the receptiveness of the endometrium is seriously compromised by the COS protocol, fresh embryo replacement should be cancelled, the embryo frozen and thawed embryo replacement should be performed under natural cycles.

The method of the present invention is also particularly suitable to understand why a patient undergoes multiple implantation failures.

The methods of the invention are particularly suitable for enhancing the pregnancy outcome of a patient. Accordingly the invention also relates to a method for enhancing the pregnancy outcome of a patient comprising:

i) assessing the endometrium receptivity of the patient by performing the method of the invention.
iii) implanting the embryo when the endometrium is considered as receptive in step i).

The embryo of step ii) may be obtained through a classical in vitro fertilization (cIVF) protocol or under an intracytoplasmic sperm injection (ICSI) protocol. The term "classical in vitro fertilization" or "cIVF" refers to a process by which oocytes are fertilised by sperm outside of the body, in vitro. IVF is a major treatment in infertility when in vivo conception has failed. The term "intracytoplasmic sperm injection" or "ICSI" refers to an in vitro fertilization procedure in which a single sperm is injected directly into an oocyte. This procedure is most commonly used to overcome male infertility factors, although it may also be used when oocytes cannot easily be penetrated by sperm, and occasionally as a method of in vitro fertilization, especially that associated with sperm donation.

Determination of the expression level of the genes as above described in Table A can be performed by a variety of techniques. Generally, the expression level as determined is a relative expression level.

More preferably, the determination comprises contacting the endometrial biopsy sample with selective reagents such as probes, primers or ligands, and thereby detecting the presence, or measuring the amount, of polypeptide or nucleic acids of interest originally in the endometrial biopsy sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the endometrial biopsy sample.

In a preferred embodiment, the expression level may be determined by determining the quantity of mRNA.

Methods for determining the quantity of mRNA are well known in the art. For example the nucleic acid contained in the endometrial biopsy sample is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Preferably quantitative or semi-quantitative RT-PCR is preferred. Real-time quantitative or semi-quantitative RT-PCR is particularly advantageous.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a particular embodiment, the methods of the invention comprise the steps of providing total RNAs extracted from an endometrial biopsy samples and subjecting the RNAs to amplification and hybridization to specific probes, more particularly by means of a quantitative or semi-quantitative RT-PCR.

In another preferred embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, an endometrial biopsy sample from a test patient, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210)

In this context, the invention further provides a DNA chip comprising a solid support which carries nucleic acids that are specific to the genes listed in table A.

Other methods for determining the expression level of said genes include the determination of the quantity of proteins encoded by said genes.

Such methods comprise contacting the endometrial biopsy sample with a binding partner capable of selectively interacting with a marker protein present in the endometrial biopsy sample. The binding partner is generally an antibody that may be polyclonal or monoclonal, preferably monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound protein in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with an antibody against the protein to be tested. An endometrial biopsy sample containing or suspected of containing the marker protein is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

Alternatively an immunohistochemistry (IHC) method may be preferred. IHC specifically provides a method of detecting targets in the endometrial biopsy sample in situ. The overall cellular integrity of the endometrial biopsy sample is maintained in IHC, thus allowing detection of both the presence and location of the targets of interest. Typically a endometrial biopsy sample is fixed with formalin, embedded in paraffin and cut into sections for staining and subsequent inspection by light microscopy. Current methods of IHC use either direct labeling or secondary antibody-based or hapten-based labeling. Examples of known IHC systems include, for example, EnVision™ (DakoCytomation), Powervision® (Immunovision, Springdale, Ariz.), the NBA™ kit (Zymed Laboratories Inc., South San Francisco, Calif.), HistoFine® (Nichirei Corp, Tokyo, Japan).

In particular embodiment, a tissue section (i.e. endometrial biopsy sample) may be mounted on a slide or other support after incubation with antibodies directed against the proteins encoded by the genes of interest. Then, microscopic inspections in the sample mounted on a suitable solid support may be performed. For the production of photomicrographs, sections comprising endometrial biopsy sample may be mounted on a glass slide or other planar support, to highlight by selective staining the presence of the proteins of interest.

Therefore IHC endometrial biopsy samples may include, for instance: (a) preparations comprising endometrial cells (b) fixed and embedded said cells and (c) detecting the proteins of interest in said endometrial biopsy samples. In some embodiments, an IHC staining procedure may comprise steps such as: cutting and trimming tissue, fixation, dehydration, paraffin infiltration, cutting in thin sections, mounting onto glass slides, baking, deparaffination, rehydration, antigen retrieval, blocking steps, applying primary antibodies, washing, applying secondary antibodies (optionally coupled to a suitable detectable label), washing, counter staining, and microscopic examination.

The invention also relates to a kit for performing the methods as above described, wherein said kit comprises means for measuring the expression levels of the genes of Table A that are indicative whether endometrium is receptive.

Another object of the invention relates to an endometrial explant obtainable from an endometrium which has been considered as receptive according to the method of the present invention.

Accordingly, said endometrial explant is characterized in that it has endometrial cells (e.g. epithelial, stromal or glandular cells) that overexpress at least one gene selected from the group consisting of MFAP5, ANGPTL1, PROK1, NLF2, LAMB3, BCL2L10, CD68, TRPC4, SORCS1, FST and KRT80. Preferably, said endometrial explant overexpresses all the genes described in Table A.

According to the present invention the endometrial explants may be thus obtained from an endometrial biopsy during which a small piece of the uterine lining of the patient was removed.

The endometrial explant according to the invention is particularly suitable for preparing endometrial coculture system for endometrium-embryo coculture during IVF.

In a particular embodiment, said endometrium-embryo coculture is autologous (the endometrial explants and the embryo result from the same patient).

Typically, the endometrial explant is treated to get a population of endometrial cells. For example, the treatment of the endometrial explant may be performed as described in US 2008064100; Eyheremendy et al., 2010; Spandorfer et al., 2004.

The obtained endometrial cells may be characterized as competent endometrial cells. As used herein the term "competent endometrial cells" refers to endometrial cells obtained from an endometrial explant according to the invention presenting overexpression at least one gene selected from the group consisting of MFAP5, ANGPTL1, PROK1, NLF2, LAMB3, BCL2L10, CD68, TRPC4, SORCS1, FST and KRT80. Preferably, said competent endometrial cells overexpress all the genes described in Table A.

Then after the population of competent endometrial cells may be co-cultured with an embryo to get a blastocyst that may be finally implanted in the patient.

Accordingly another object of the invention relates to a method of growing an embryo to a blastocyst stage of development comprising the step of coculturing said embryo in the presence of a population of competent endometrial cells as above defined.

In a particular embodiment the method of growing an embryo to a blastocyst stage of development comprises step of coculturing said embryo on a cell culture surface coated with a layer of competent endometrial cells obtained as above defined.

The term "cell culture surface" or "cell culture matrix" refers to every type of surface or matrix suitable for cell culture. The term "cell culture surface" includes but is not limited to tissue culture plate, dish, well or bottle. In a particular embodiment, the culture surface is plastic surface of the culture plate, dish, well or bottle. The cell culture surface is to be compatible with the coating of competent endometrial cells. According to an embodiment of the invention, the cell culture surface is selected in the manner that competent endometrial cells may naturally adhere on it. Various materials of cell culture surface may be selected. Examples of such materials include but are not limited to tissue culture dishes or dishes coated with collagen.

Typically, to obtain a layer of competent endometrial cells on a cell culture surface, the competent endometrial cells are first coated on the cell culture surface with a culture medium containing collagen. After a sufficient time for allowing adhesion of competent endometrial cell on the cell culture surface, the culture medium containing collagen is removed and replace by a medium that allows expansion of said competent endometrial cells.

In a particular embodiment, competent endometrial cells are previously treated to stop their proliferation before to in be in contact with the embryo. Therefore, the competent endometrial cells are inactivated by gamma irradiation or with a cell cycle blocking agent.

In another embodiment, the competent endometrial cells may be immortalized to get competent endometrial cell lines.

Conditions (e.g. temperature, $CO_2$ levels . . . ) and culture medium for endometrium-embryo coculture are well known in the art and are described for example in Eyheremendy et al., 2010 and Spandorfer et al., 2004.

The endometrial coculture system of the present invention is thus particularly suitable for increasing the in vivo implantation potential of an in vitro fertilization embryo. "Implantation potential" is the ability of the embryos to implant in the uterus. Accordingly the present invention relates to a method for increasing the in vivo implantation potential of an in vitro fertilization embryo. This method includes carrying out one of the above-described embodiments for growing an embryo to a blastocyst stage of development, such that complete hatching of the embryo in culture is achieved or hatching is enhanced, compared to other IVF methods. In accordance with certain embodiments of this method, the balstocyst is then introduced into the uterus of a mammalian host, such than enhanced implantation of the embryo is achieved. In some embodiments, complete hatching of the embryo in vitro correlates with establishment of a viable pregnancy. Typically, once a patient has been deemed an appropriate candidate for the procedure, she undergoes the method of the invention for determining endometrium receptivity. If the endomtrium is considered receptive an endometrial biopsy is performed by during which a small piece of her uterine lining is removed to get an endomtrium explants as describe supra. The endomtrium explants may be then sent to a lab or company, where it is treated, purified and frozen. The patient then undergoes a typical IVF cycle and is given medication to stimulate egg growth in her ovaries. The patient's eggs are retrieved and mixed with the sperm. At this time, the lab begins thawing and growing her endometrial cells derived from the endometrium explants as above prepared. Once fertilization is confirmed, the patient's embryos are cocultured endometrial cells. When blastocyst stage is reached, patient's embryo(s) are transferred into her uterus for implantation and pregnancy.

In some embodiments of the present invention, a method of increasing the live birth potential of an in vitro fertilized mammalian embryo is also provided. "Live birth potential" refers to the ability of an embryo to yield a live birth. The method comprises growing an embryo to a blastocyst stage of development, as described above, such that enhanced hatching potential or complete hatching of the embryos in culture is achieved. The blastocyst is then transferred to the uterus of a mammalian host; and the embryo is allowed to implant and grow in vivo, such that the ability of the embryo to yield a live birth is enhanced relative to that of an embryo that is not cultured according to the invention.

The method of the invention is also particularly suitable for limiting multiple pregnancies because it can provides a higher implantation rate and therefore fewer embryos could be transferred at each cycle, resulting in a decreased incidence of multiple pregnancies.

The invention will be further illustrated by the following examples and figures. However, these examples and figures should not be interpreted in any way as limiting the scope of the present invention.

FIGURES

Figure 2:
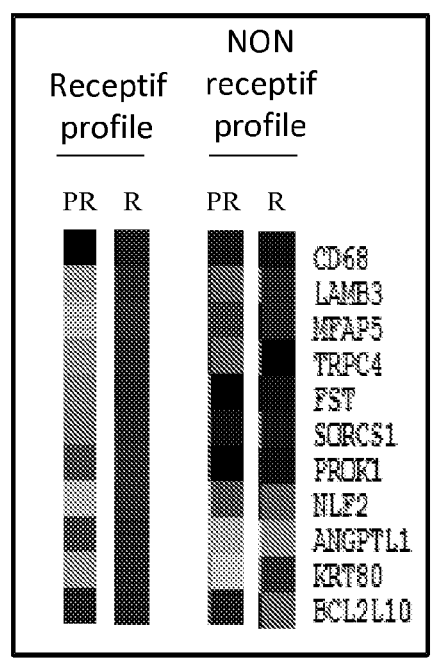
Figure 3:
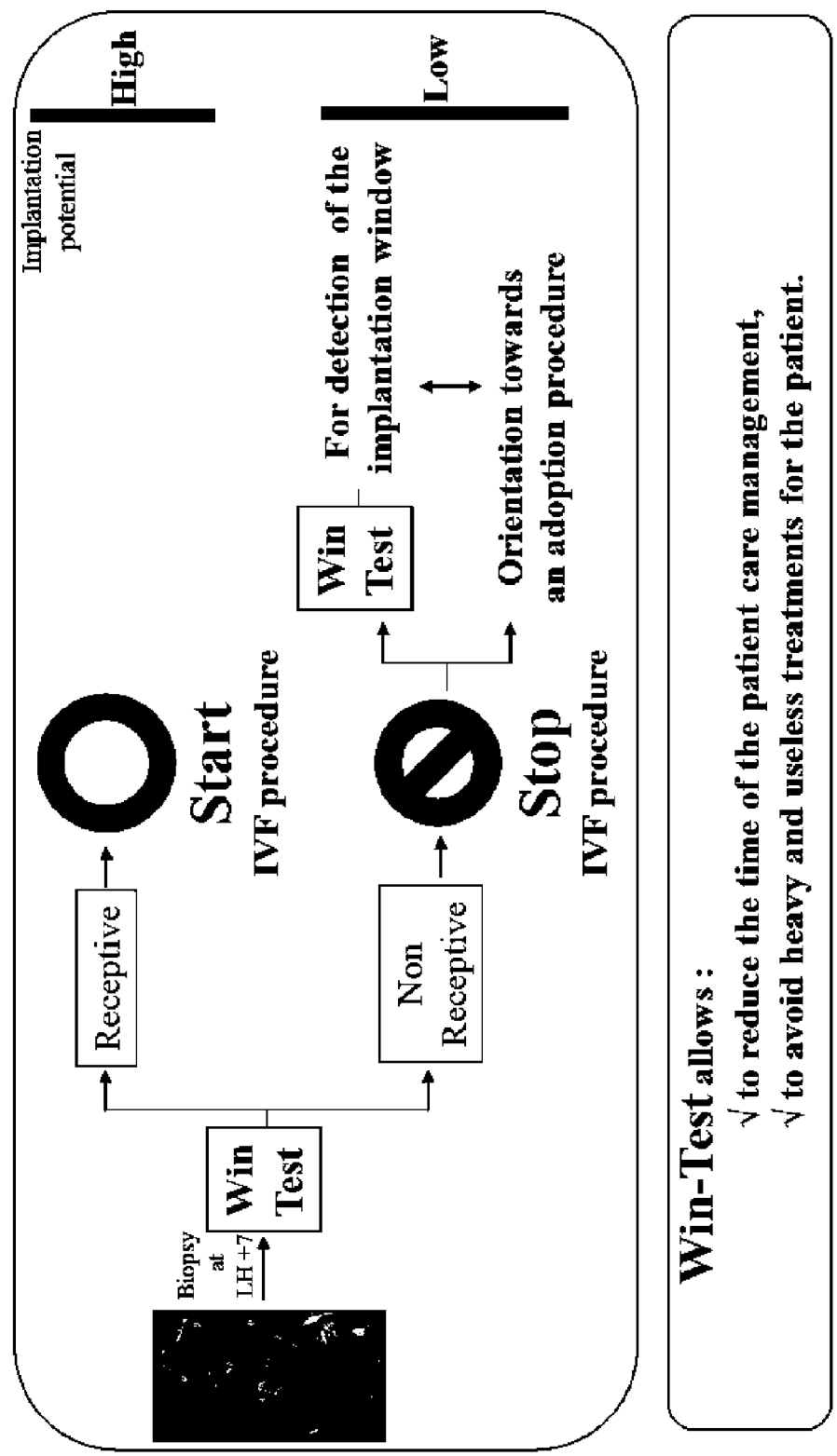
Figure 4:
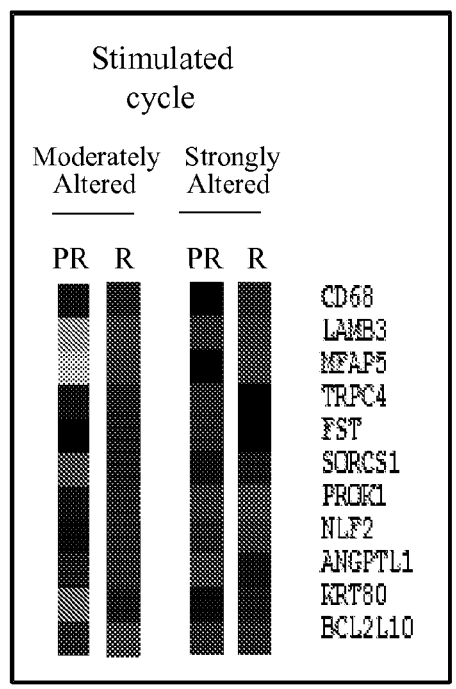
Figure 5:
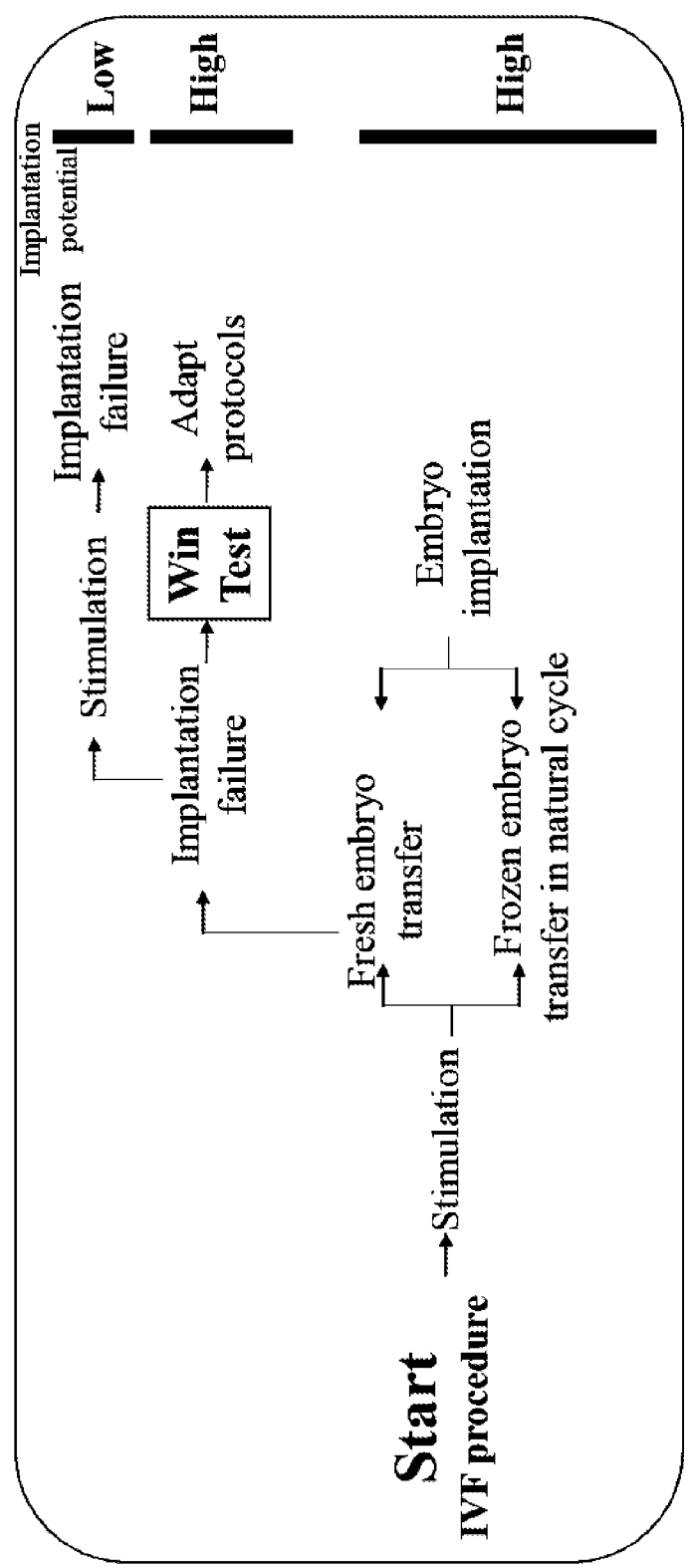
Figure 6:
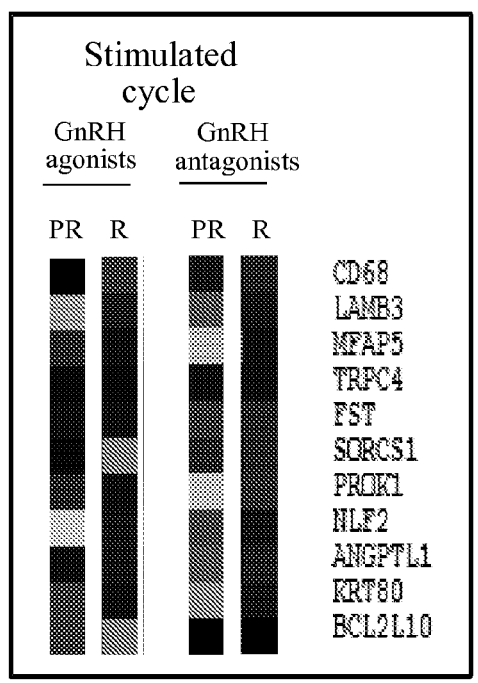
Figure 7:
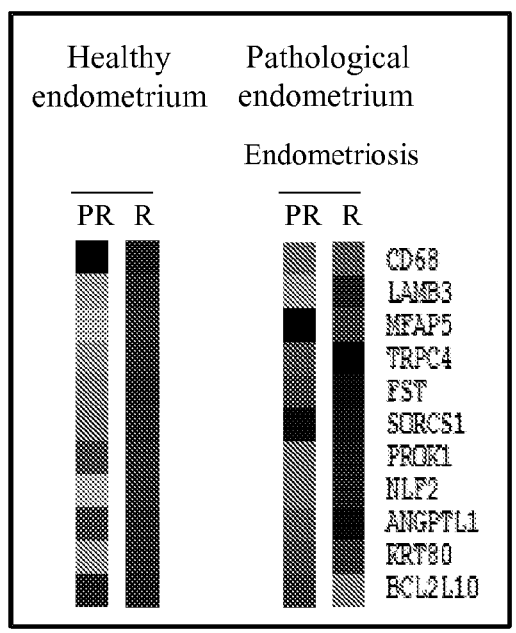
Figure 8:
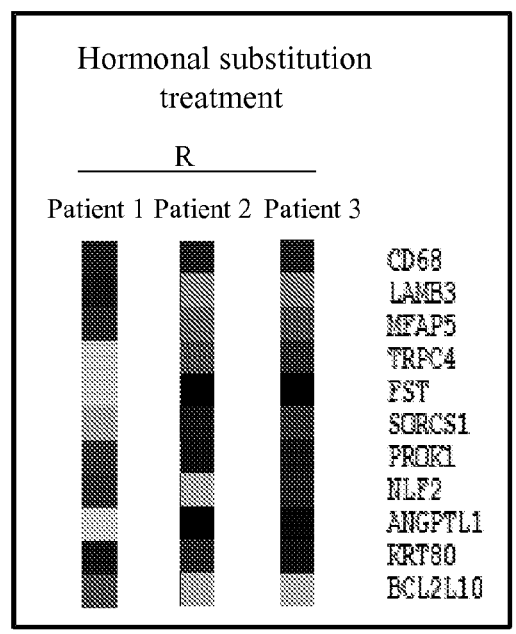

FIG. 1: Identification of new bio-markers of endometrial receptivity.
FIG. 2: Win Test (window implantation test) during the implantation window under natural cycle.
FIG. 3: Consequences for the patient care management during IVF procedure.
FIG. 4: Win Test to check the receptive status of patients between natural and stimulated cycles.
FIG. 5: Consequences for the patient care management during IVF procedure.
FIG. 6: Win Test to check the receptive status of patients with multiple implantation failures.
FIG. 7: Win Test to check the receptive status of infertile women with gynecological diseases.
FIG. 8: Win Test to check the impact of hormonal substitution treatment during endometrial preparation in recipient patients for oocyte donation.

EXAMPLES

Example 1

Material & Methods

Identification of New Bio-Markers of Endometrial Receptivity (Haouzi et al., 2009) (FIG. 1)

Patient Characteristics and Endometrial Biopsies:

This project has received institutional review board approval. The study population included 31 patients (age 30.4 years±3.2), recruited after written informed consent. All patients had normal serum FSH, LH, estradiol and AMH levels on day 3 and were normal responders during a previous first ICSI attempt. They were referred for ICSI for male infertility factor. During the same natural cycle that preceded a second ICSI attempt, two endometrial biopsies were obtained in all women at day 2 (LH+2) and day 7 (LH+7) after the LH peak. The LH surge was estimated by patient herself according to the first day of their menstruation. Histologic analysis was not performed to verify that the LH timing was accurate. Therefore, the possibility for a delay of one day from the first day of the menstruation cannot be excluded. Each biopsy sample was washed in PBS and frozen at −80° C. in RLT RNA extraction buffer (RNeasy kit, Qiagen, Valencia, Calif., USA).

Complementary RNA (cRNA) Preparation and Microarray Hybridization:

Total RNA (100 ng) was used to prepare twice amplified labeled cRNA for hybridization to HG-U133 plus 2.0 GeneChip pangenomic oligonucleotide arrays (Affymetrix, Santa Clara, Calif., USA) as described in (Haouzi et al., 2009).

Microarray Data Analyses:

HG-U133 plus 2.0 arrays contain 54,675 oligonucleotide probe sets, which correspond to ≈30,000 unique human genes or predicted genes. Array analysis was performed with the GeneChip Operating Software 1.2 (Affymetrix) to measure significant RNA detection (detection call "present" or "absent") and to evaluate the signal intensity for each probe set.

Bioinformatics and in Silico Analyses:

The Significant Analysis of microarrays (SAM, Stanford University, USA, Tusher et al. 2001) was used to identify genes whose expression varied significantly between the two sample groups, LH+2 (n=31) and LH+7 (n=31). SAM provides mean or median fold change values (FC) and a false discovery rate (FDR) confidence percentage based on data permutation.

To compare profile expression of endometrial samples (n=62) from the LH+2 and LH+7 groups, we performed an unsupervised classification with both principal component analysis (PCA) and hierarchical clustering (Eisen et al., 1998; de Hoon et al., 2004). The PCA involved original scripts based on the R statistics software through the RAGE web interface (http://rage.montp.inserm.fr) (Rème et al., 2008). Hierarchical clustering analysis based on the expression levels of varying probes were performed with the CLUSTER and TREEVIEW software packages. Genetic expression profiles were analyzed with the RAGE supervised analysis module, using a non parametric Mann Whitney U test with multiple testing corrections and were confirmed with the SAM software.

Predictor Construction:

This 3-step process extensively described elsewhere (Rème et al., 2008) has been modified for paired samples. Affymetrix detection calls were used throughout with only two levels of expression, "Present" as 1 and "Else" as 0. As recommended by others, probe sets were filtered by selecting half the size of a sample class as the minimal number of present calls across all samples. Probe sets with poorly informative signals were further eliminated using a minimal variation coefficient of 40%, leading to a final 16,130 probe sets out of a 54,613-probe sets U133P chip.

Reduction of the data dimensionality was achieved by comparing each probe set distribution in sample groups considered as multiple drawings of a two-stage criterion (presence=1, else=0). Briefly, to account with the paired situations (LH2 and LH7) for one patient, a probe set vector was constructed whose values are either 0 if both situations lead to the same call and 1 if they differ. This vector is then compared to the null vector using a $\chi^2$ test, with a multiple testing corrected P value resulting in a 200-500 probe set list, subsequently used for supervised analysis. The capacity of such a list to separate sample classes is evaluated as described previously by maximizing the significance of sample to sample comparisons using a $\chi^2$ test with Bonferroni correction for multiple testing and Yates correction for small sample numbers in two class comparisons. If the significance threshold is reached, the samples are not in the same class. This is repeated for comparison of each class sample paired to any sample of the other class and the initial number and strength of non-significant comparisons can be determined. Reducing the list is achieved by minimizing the number of non-significant comparisons by successive deletions of the probe set giving the best improvement. The process stops when no criterion can be further improved by probe set removal, the remaining list being the predictor.

For leave-one-out cross-validation, each sample pair in turn is removed, and the whole process of dimensionality reduction and predictor building is run with Bonferroni correction on the remaining samples as described for initial classes. Each predictor build in this way is tested for its capacity to generate misclassification errors when the left-out sample is returned to its class, where the number of non-significant comparisons should be 0.

Results

Gene Expression Profile as a Function of the Endometrium Receptivity:

Selection using a variation coefficient (≥40%) and the Absent/Present "detection call" (presence in at least 15 samples) between LH+2 and LH+7 samples was first performed, delineating≈16,200 probe sets. Then, we performed a SAM analysis between the LH+2 and the LH+7 sample groups (LH+2 versus LH+7, paired sample analysis). 1012 genes were significantly modulated between these two groups, including 945 up-regulated genes and 67 down-regulated genes in the LH+7 sample group (fold change≥2 and a P-value<0.05).

Validation of the Predictor List:

We first, performed a PCA analysis of our LH+2 and LH+7 samples with the predictor list (comprising 60 probe sets) established before as described in materials and methods with a 6% leave-one-out cross-validation error for a P-value≤0.01. 75% of LH+7 samples were separated from the other samples in this PCA using the first two dimensions, representing 52% of the data information. We then tested our predictor list on the Talbi et al. (2006) samples, which consisted in three early-secretory samples and eight mid-secretory samples. The PCA analysis of these independent samples with our predictor list allows a distinct separation using the first two dimensions, between the two sample groups (LH+2 and LH+7), representing 53% of the data information.

New Candidate Gene Selection of the Implantation Window:

To identify new markers of endometrium receptivity, we have first intersected our gene list significantly modulated between the LH+2 and LH+7 sample groups with those from four other transcriptomic studies which compared the same natural endometrium cycle phases (Carson et al., 2002; Riesewijk et al., 2003; Mirkin et al., 2005; Talbi et al., 2006) to identify a list of genes comprising 797 genes specifically modulated during the implantation window and exclusive to the present study. We performed a hierarchical clustering with the same data (797 genes). This list of genes allowed the separation of the two endometrium sample groups. Interestingly, the majority of these genes were up-regulated during the implantation window (746 up-regulated genes, 51 down-regulated genes).

To select candidate genes of the implantation window, we then have compared our list of genes specifically modulated during the implantation window and exclusive to our study with the list of predictor. We have selected 10 new genes predicting endometrium receptivity, not listed in reports by microarray analysis. Among these new genes, only 4 genes have been published in Haouzi et al. (2009). These published new markers are MFAP5 (microfibrillar associated protein 5), ANGPTL1 (angiopoietin-like 1), EG-VEGF also called PROK1 (endocrine-gland-derived vascular endothelial growth factor or prokineticin 1) and NLF2 (nuclear localized factor 2) and are all over-expressed during the implantation window in microarray analyses respectively by a factor of 37, 12.6, 10.2, and 22.5. In addition, a gene found in two other microarray analysis, established by Riesewijk et al. (2003) and Talbi et al. (2006), and in our study was chosen as a positive control of human endometrium receptivity. This gene is LAMB3 and is over-expressed by a factor 20.4 in our study, and a factor 15 and 6.6 in the Riesewijk and Tablbi's studies respectively. The six unpublished genes were BCL2L10 (BCL2-like 10), CD68, TRPC4 (transient receptor potential cation channel, subfamily C, member 4), SORCS1 (sortilin-related VPS10 domain containing receptor 1), FST (follistatin), and KRT80 (keratin 80) which were also over-expressed during the implantation window by a factor 4.7, 5.3, 7.7, 9, 9 and 14.6 respectively.

Discussion:

Our microarray analysis identified a series of biomarkers of the human endometrial receptivity among which we selected 11 candidates: LAMB3, MFAP5, ANGPTL1, EG-VEGF (PROK1), NLF2, FST, KRT80, BCL2L10, CD68, TRPC4, and SORCS1.

In the baboon endometrium, laminin expression is increased at the implantation site and throughout the endometrium, suggesting a role of this extracellular matrix component in the endometrium receptivity. MFAP5, also called MAGP2, was also over-expressed in our LH+7 sample group. This gene encodes a microfibril-associated glycoprotein which is a component of microfibrils, an important structural component of elastic tissues such as vasculature. By interacting with both extracellular matrix, such as collagen, and cell-associated proteins, such as integrins, this protein is therefore positioned to potentially modulate cell matrix interactions and to participate in cell signaling pathways. Moreover, it has been recently suggested that MFAP5 has a role in Notch signaling activation, a pathway involved in vasculature during embryogenesis, development and normal homeostasis.

We also found that two members of the vascular endothelial growth factor family, EG-VEGF and ANGPTL1, were over-expressed in human endometrium during the implantation window. Endocrine gland-derived vascular endothelial growth factor (EG-VEGF), also called PROK1, is a newly identified angiogenic and permeability enhancing factor predominantly expressed in steroidogenic tissues. EG-VEGF is also expressed in the normal peri-implantation endometrial samples from patients of reproductive ages, and rarely detected in the endometrial samples from the post-menopausal patients and patients with endometrial carcinoma. EG-VEGF is predominantly expressed in the glandular epithelial cells with a peak protein expression at the mid luteal phase of the menstrual cycle. The coexistence of EG-VEGF and its receptor, PROKR1, in human endometrium supports the idea that EG-VEGF may regulate proliferation, angiogenesis and permeability and induce the formation of endothelial fenestration. ANGPTL1 (angiopoietin-like 1) is a member of the angiopoietin related protein family. In in vitro studies, ANGPTL1 has anti-apoptotic activities through the phosphatidylinositol 3-kinase/Akt pathway and regulates angiogenesis. In the ovariectomized ewe model, ANGPTL1 mRNA is increased after estradiol treatment. In our study, we observed an over-expression of ANGPTL1 gene during the implantation window of endometrium.

In our microarray data and quantitative PCR analysis, NLF2 gene expression was strongly expressed in the LH+7 sample group, suggesting that it has a role in endometrium remodeling during the implantation window. Invasion into the endometrial stroma is facilitated by inflammation. NLF2, also called C2CD4B (C2 calcium-dependent domain containing 4B), was recently identified as a nuclear factor and as a member of a family of regulatory genes that play a role in endothelial cell inflammation. Initially identified in genome wide array screen of human microvascular endothelial cells treated with interleukin 1beta, NLF2 is probably part of the signaling pathway causing changes in cell architecture and adhesion in endothelial cell inflammation.

Follistatin (FST) is a single-chain gonadal glycoprotein that specifically inhibits follicle-stimulating hormone (FSH) release. Follistatin has been previously described to be present in the endometrium and was localized in stromal and epithelial cells. Secretion of FSH from epithelial cells might be important for restricting the bioavailability of activin within the uterine lumen. Follistatin might also have activin independent effects and can also bind other members of the TGF-beta superfamily, including inhibin and certain members of the BMP (bone morphogenetic protein) family. In human uterus, the expression patterns of the gene encoding FST is consistent with a role in decidualization, a key event for blastocyst implantation and successful pregnancy outcome after IVF. In addition, it was recently reported a decreased expression of FST in epithelial cells in the endometrium of women with implantation failure after IVF compared with control fertile women, reinforcing the notion that FST may play a role in the implantation. This finding was consistent with the present study showing an over-expression of the FST gene expression in the human receptive endometrium.

We also identified the keratine 80 (KRT80) gene as a biomarker of the implantation window as judged by their over-expression in the receptive endometrium compared with the pre-receptive endometrium. Keratins are intermediate filament proteins responsible for the cellular architecture of epithelial cells, which is necessary to achieve specific function. These proteins are required on a cellular level for phagocytosis, pinocytosis, cell adhesion, cell motility, subcellular organization and cell division. On a tissue level, structural proteins are necessary for contraction and intact epithelium. Structural proteins may also play a role in intracellular trafficking through the microtubule network.

Apoptosis plays a critical role in maintaining cellular homeostasis during the menstrual by eliminating senescent cells from the functional layer of the uterine endometrium during the late secretory and menstrual phase of the cycle. Apoptosis was detected in the glandular epithelium of late secretory and menstruating endometrium, while very little apoptosis was detected during the proliferative phase or at the beginning of the secretory phase. Members of the Bcl2 family of proteins are fundamental elements in the pathways that control apoptosis and act as pro- and anti-apoptotic regulators. Among them, BCL2L10 which has been previously shown to suppress cell apoptosis, was found, in the present study, to be over-expressed in the human receptive endometrium in comparison with the pre-receptive endometrium. This finding was coherent with the period of apoptosis detection through the menstrual cycle.

Changes in the number and distribution of macrophages and dendritic cells could point to a possible role of these immunocompetent cells in implantation and success of early pregnancy. In the present study, we reported the over-expression of the CD68 gene in the receptive endometrium which encodes a transmembrane glycoprotein highly expressed by human monocytes and tissue macrophages. This type I integral membrane protein binds to tissue- and organ-specific lectins or selectins which are abundantly expressed during the implantation window.

TRPC4 is one members of the transient receptor potential cation channel family which may facilitate store operated calcium entry (SOCE) to calcium signaling in the human myometrium. TRPC4 mRNA and protein have been previously described to be over-expressed in term pregnant human myometrium. However, we reported for the first time an over-expression of this gene in the receptive endometrium in comparison with the pre-receptive endometrium, suggesting a potential role of TRPC4 in implantation process.

SORCS1, which is over-expressed in this study during the human implantation window, is the first identified member of a subgroup of the mammalian Vps10p-domain receptor family that comprises an N-terminal Vps10p-D (named after the yeast vacuolar protein sorting 10 protein), a leucine-rich domain, a single transmembrane domain, and a short cytoplasmic domain. Functions of this gene were not elucidated because it has been reported that sorCS1 was synthesized as a proprotein that is cleaved to mature forms in the trans-Golgi network and expressed in three isoforms with different cytoplasmic domains capable of mediating different trafficking of the receptor.

In conclusion, our data using analysis of transcriptomic pattern of endometrium shift between the pre-receptive and receptive stages could open new perspectives, especially in patients with multiple implantation failures. Analysis of these biomarkers would allow (i) the evaluation of the receptive status of endometrium of all patients attending for an IVF procedure, and consequently, the identification of altered endometrial profiles in some normal responder patients. The information given by these biomarkers during a natural cycle could then be used subsequently to adapt the IVF protocol in patients with poor implantation.

Example 2

Exemplary Profile of Patient with Endometrial Receptivity Assessment in Natural Cycle According to an embodiment of the invention, assessing the endometrium receptivity of a patient comprise a first step consisting of measuring the mRNA expression of the 11 bio-markers (Win Test: window implantation test) during the implantation window (LH+7) under natural cycle (FIG. 2) and a second step comprising two scenarios: (i) the patient presents a delay of her implantation window and, in this case, Win Test could help in the detection of the implantation window; (ii) Win test could allow to identify patients never presenting a receptive endometrium and, in this case, they are oriented towards an adoption procedure (FIG. 3: Consequences for the patient care management during IVF procedure).

Example 3

Exemplary Profile of Patient with Endometrial Receptivity Assessment in Stimulated Cycle According to one embodiment of the invention, the comparisons of gene expression from the same patients between natural and stimulated cycles revealed endometrial profiles associated either with a moderately altered receptivity in most cases (86%) or a strongly altered receptivity during the COH protocol in a few cases (14%) (FIG. 4). The invention provide two consequence of the Win Test: i) Fresh embryo replacement could be reconsidered during IVF procedure. Embryos freezing enable the IVF attempt to be saved and the embryo transfer can be done later during a natural cycle; ii) For patients with multiple implantation failures, analysis of the endometrial profile (Win test) could reveal a strongly altered profile during COH protocols, prompting the clinician to either adapt the IVF stimulation protocol or to perform embryo transfer later during a natural cycle or to orient the patient in a adoption procedure (FIG. 5).

Example 4

Win Test as Means to Set Up "À La Carte" "the Adequate" Treatments

The inventors have described that both protocols (GnRH antagonists and agonists) affected endometrial receptivity, but differently. The question for the patient care management is "What protocols used?" in regard of the different GnRH analogue effects and the heterogeneous responses of patients during treatments.

According to one embodiment of the invention, for patients with multiple implantation failures, analysis of the endometrial profile (Win test) could help the clinician to adapt the IVF stimulation protocol (FIG. 6).

Example 5

Win Test to Check the Receptive Status of Infertile Women with Gynecological Diseases According to one embodiment of the invention, Win Test could be used as markers to evaluate endometrial receptivity in women with gynecological diseases. The potential relationship between several gynecological diseases (for example, endometriosis and adenomyosis) and abnormal endometrial receptivity as a possible cause of sub-fertility in these patients can be tested with Win Test (FIG. 7).

Example 6

Win Test to Check the Impact of Hormonal Substitution Treatment During Endometrial Preparation in Recipient Patients for Oocyte Donation According to one embodiment of the invention, Win test can be used to ameliorate hormonal treatments for endometrial maturation. Win Test reveals an altered endometrial profile at the time of the implantation window in oocyte recipient patients under hormonal substitution treatment (estrogen and progesterone treatments) compared with natural cycle (FIG. 8).

"Win Test" (comprising a set of 11 genes issued from both their exclusive gene list and their list of predictor) is a diagnostic tool particularly relevant as several genes issued from their exclusive list have been found by other studies at proteomic levels (Table B).

REFERENCES

Throughout this application, various references describe the state of the art to which this invention pertains. The disclosures of these references are hereby incorporated by reference into the present disclosure.

Carson D D, Lagow E, Thathiah A, Al-Shami R, Farach-Carson M C, Vernon M, Yuan L, Fritz M A, Lessey B. (2002). Changes in gene expression during the early to mid-luteal (receptive phase) transition in human endometrium detected by high-density microarray screening. Mol Hum Reprod. 8(9):871-9.

De Hoon, M. J., Imoto, S., Nolan, J. and Miyano, S. Open source clustering software. Bioinformatics 2004; 20:1453-4.

Eisen M B, Spellman P T, Brown P O, Botstein D. Cluster analysis and display of genomewide expression patterns. Proceedings of the National Academy of Sciences of the United States of America 1998; 95:14863-8.

Eyheremendy V, Raffo F G, Papayannis M, Barnes J, Granados C, Blaquier J. (2010) Beneficial effect of autologous endometrial cell coculture in patients with repeated implantation failure. Fertil Steril. 93(3):769-73.

Haouzi D, Mahmoud K, Fourar M, Bendhaou K, Dechaud H, De Vos J, Rème T, Dewailly D, Hamamah S. Identification of new biomarkers of human endometrial receptivity in the natural cycle. Hum Reprod. 2009; 24:198-205.

Mirkin S, Arslan M, Churikov D, Corica A, Diaz J I, Williams S, Bocca S, Oehninger S. (2005). In search of candidate genes critically expressed in the human endometrium during the window of implantation. Hum Reprod. 20(8):2104-17.

Rème T, Hose D, De Vos J, Vassal A, Poulain P O, Pantesco V, Goldschmidt H, Klein B. A new method for class prediction based on signed-rank algorithms applied to Affymetrix microarray experiments. BMC Bio informatics 2008; 11:9-16.

Riesewijk A, Martín J, van Os R, Horcajadas J A, Polman J, Pellicer A, Mosselman S, Simón C. (2003). Gene expression profiling of human endometrial receptivity on days LH+2 versus LH+7 by microarray technology. Mol Hum Reprod. 9(5):253-64.

Spandorfer S D, Pascal P, Parks J, Clark R, Veeck L, Davis O K, Rosenwaks Z. (2004) Autologous endometrial co-cul-

TABLE B

Correlation between gene and protein expression levels which were referred as biomarkers of endometrial receptivity

| | | Transcriptonic studies | | | | | | Proteomic studies | |
| --- | --- | --- | --- | --- | --- | --- | --- | --- | --- |
| Name | Symbol | Carson et al. (2002) | Riesewijk et al. (2003) | Mirkin et al. (2005) | Talbi et al. (2006) | Huouzi et al. (2009a) | Diaz-Gimeno et al. (2011) | Li et al. (2006) | Dominguez et al. (2009) |
| Annexin A4 | ANXA4 | | x4 | x6.5 | x4.9 | x2.6 | x4.7 | x2.1 | x1.9 |
| Annexin A2 | ANXA2 | | x4 | x5.6 | x2 | | | | x2.1 |
| Monoamine oxidase A | MAOA | | | x15 | | x9.9 | x8.4 | | x3.4 |
| Transgelin 2 | TAGLN | | | x6 | | x5.9 | | | x1.7 |
| L-plastin | LCP1 | | | | x2.6 | x1.6 | | | x1.6 |
| Progesterone receptor membrane component 1 | PGRMC1 | | | | | x−1.8 | | | x−2.4 |
| Stathmin 1 | STMN1 | | | | x−3.2 | | | | x−2.2 |
| Apolipoprotein L2 | APOL2 | | | | | x2.4 | | | x3.7 |
| Aldehyde dehydrogenase 1 family, member A3 | ALDH1A3 | | | | | x16.5 | | | x1.8 |
| S100 calcium binding protein A10 | S100A10 | | | | | x3.5 | | | x4.8 | ture in patients with IVF failures: outcome of the first 1030 cases. J Reprod Med 49(6), 463-7.

Talbi S, Hamilton A E, Vo K C, Tulac S, Overgaard M T, Dosiou C, Le Shay N, Nezhat C N, Kempson R, Lessey B A, Nayak N R, Giudice L C. (2006). Molecular phenotyping of human endometrium distinguishes menstrual cycle phases and underlying biological processes in normo-ovulatory women. Endocrinology. 147(3):1097-121.

The invention claimed is:

1. A method of obtaining a blastocyst, comprising the steps of:
  a) obtaining an endometrial biopsy sample from a patient;
  b) measuring, in said endometrial biopsy sample, the expression level of each of the eleven genes MFAP5, ANGPTL1, PROK1, NLF2, LAMB3, BCL2L10, CD68, TRPC4, SORCS1, FST and KRT80;
  c) comparing the expression level of each of the eleven genes in the endometrial biopsy sample with control expression levels of the eleven genes from endometrial biopsy sample obtained from a non-receptive endometrium;
  d) assessing the endometrium of the patient as being receptive when all of said eleven genes are overexpressed compared to the control;
  e) preparing competent endometrial cells from an endometrial explant from said patient having a receptive endometrium as determined in step d); and
  f) coculturing the competent endometrial cells with an embryo to obtain a blastocyst.

2. A method of implanting a blastocyst in a female undergoing in vitro fertilization (IVF), comprising the steps of:
  a) obtaining an endometrial biopsy sample from said female;
  b) measuring, in said endometrial biopsy sample, the expression level of each of the eleven genes MFAP5, ANGPTL1, PROK1, NLF2, LAMB3, BCL2L10, CD68, TRPC4, SORCS1, FST and KRT80;
  c) comparing the expression level of each of the eleven genes in the endometrial biopsy sample with control expression levels of the eleven genes from endometrial biopsy sample obtained from a non-receptive endometrium;
  d) assessing the endometrium of the female as being receptive when all of said eleven genes are overexpressed compared to the control;
  e) preparing competent endometrial cells from an endometrial explant from said female having a receptive endometrium;
  f) coculturing the competent endometrial cells with an embryo to obtain a blastocyst; and
  g) implanting the blastocyst in said female having a receptive endometrium as determined in step d).

3. A method of implanting an embryo in a female undergoing in vitro fertilization (IVF), comprising the steps of:
  a) obtaining an endometrial biopsy sample from said female;
  b) measuring, in said endometrial biopsy sample, the expression level of each of the eleven genes MFAP5, ANGPTL1, PROK1, NLF2, LAMB3, BCL2L10, CD68, TRPC4, SORCS1, FST and KRT80;
  c) comparing the expression level of each of the eleven genes in the endometrial biopsy sample with control expression levels of the eleven genes from endometrial biopsy sample obtained from a non-receptive endometrium;
  d) assessing the endometrium of the female as being receptive when all of said eleven genes are overexpressed compared to the control;
  e) implanting an embryo in said female having a receptive endometrium as determined in step d).

4. The method of claim 3, wherein the embryo is autologous.

\* \* \* \* \*